United States Patent
Kunze

(10) Patent No.: US 7,986,762 B2
(45) Date of Patent: Jul. 26, 2011

(54) METHOD FOR RECORDING AN EXAMINATION OBJECT

(75) Inventor: Holger Kunze, Bubenreuth (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 12/861,908

(22) Filed: Aug. 24, 2010

(65) Prior Publication Data
US 2011/0051887 A1 Mar. 3, 2011

(30) Foreign Application Priority Data
Aug. 25, 2009 (DE) .................. 10 2009 038 787

(51) Int. Cl.
*A61B 6/00* (2006.01)
(52) U.S. Cl. .................................. 378/11; 378/4
(58) Field of Classification Search .............. 378/4, 11
See application file for complete search history.

(56) References Cited

U.S. PATENT DOCUMENTS

| | | | |
|---|---|---|---|
| 5,740,224 A * | 4/1998 | Muller et al. | 378/11 |
| 6,435,714 B1 * | 8/2002 | Bruder | 378/196 |
| 7,110,487 B2 * | 9/2006 | Baba et al. | 378/11 |
| 7,177,455 B2 * | 2/2007 | Warp et al. | 382/132 |
| 7,558,368 B2 * | 7/2009 | Klingenbeck-Regn | 378/41 |
| 7,796,723 B2 * | 9/2010 | Harer et al. | 378/26 |
| 2006/0039537 A1 * | 2/2006 | Strobel | 378/197 |
| 2008/0089468 A1 * | 4/2008 | Heigl et al. | 378/20 |
| 2008/0181367 A1 * | 7/2008 | Heigl et al. | 378/207 |
| 2009/0252287 A1 * | 10/2009 | Boese et al. | 378/17 |

FOREIGN PATENT DOCUMENTS
DE 102006041033 A1 3/2008
DE 102007003877 A1 7/2008

OTHER PUBLICATIONS

Ge Wang, "X-ray micro-CT with a displaced detector array", American Association of Physicists in Medicine, Med. Phys. 29 (7), Jul. 2002, pp. 1634-1636.
Dennis L. Parker, "Optimal short scan convolution reconstruction for fanbeam CT", Medical Physics, vol. 9, No, 2, Mar./Apr. 1982, pp. 254-257.

* cited by examiner

*Primary Examiner* — Edward J Glick
*Assistant Examiner* — Alexander H Taningco

(57) ABSTRACT

A method is provided for recording an examination object using an x-ray recording system having an x-ray source and an x-ray detector rotatable about a common axis of rotation. X-ray detector is displaced in a first direction enclosing a first angle k between a perpendicular bisector from x-ray source to x-ray detector and a plane running through x-ray source and containing the axis, k≠0. First x-ray images are recorded in angular positions of x-ray source and x-ray detector displaced in the first direction in a first rotation. X-ray detector is displaced in a second direction enclosing a second angle m between the bisector and the plane, m≠0 and is on an opposite side from k. Starting points of the rotations are differed by an angle of displacement $$\beta_0 = \frac{k+m+d}{2},$$

where d is the detector fan angle. Starting points and finishing points of the rotations are spanned by $\pi + \beta_0$.

5 Claims, 4 Drawing Sheets

METHOD FOR RECORDING AN EXAMINATION OBJECT

CROSS REFERENCE TO RELATED APPLICATIONS

This application claims priority of German application No. 10 2009 038 787.0 filed Aug. 25, 2009, which is incorporated by reference herein in its entirety.

FIELD OF THE INVENTION

The invention relates to a method for recording an examination object comprising an x-ray recording system which can be rotated about a shared axis of rotation and comprises an x-ray source and an x-ray detector.

BACKGROUND OF THE INVENTION

In addition to the known computer tomography, x-ray projections disposed on a circle can be recorded with the aid of C-arm x-ray devices and used for a tomography reconstruction. Since flat panel detectors with a maximum size of 30×40 cm are generally used here, the size of the flat panel detector thus represented a limitation in the past. This was solved in that the movement of the C-arm in novel C-arm x-ray devices takes place by means of an industrial robot. New and also complicated recording movements are herewith possible, e.g. the so-called Large Volume Acquisition. The C-arm is herewith rotated twice about the examination object, once so that the perpendicular bisector of the side is moved by the x-ray detector onto the x-ray detector to a plane running toward the x-ray source and containing the axis of rotation and a second time so that the perpendicular bisector of the side is shifted to the right relative to the plane. The projections, in which the x-ray source is located at the same location, are then merged for reconstruction purposes to form a large virtual projection. The plurality of virtual projections is then used with a standard reconstruction method, like the filtered back projection, for volume calculation purposes.

To achieve a minimal scanning time and apply as small an x-ray dose as possible, rotations of less than 360° are frequently (easily) implemented. As a minimal scanning range per rotation (in total displaced once to the left and once to the right) projections are recorded in an angular range of 180°+ fan angle of the virtual x-ray detector (combination of the x-ray detector in the position displaced to the left and the position displaced to the right) in relation to the x-ray source.

From the article by G. Wang: "X-ray micro-CT with a displaced detector array", Med. Phys. 29 (7), pp. 1634-1636, July 2002, it is known that an increase in the measurement field can also be achieved if an x-ray detector displaced by less than 50% to the side is rotated in an angular range of 360° once about the examination object. The applied x-ray dose can as a result likewise be reduced. This method requires, however, that the x-ray device can record through 360° when the x-ray detector is displaced, which—despite all the flexibility of an industrial robot—is frequently not the case, in particular where patients are involved.

SUMMARY OF THE INVENTION

It is the task of the invention to provide a large-volume method for recording a large and/or difficult-to-access examination object which will keep the radiation loading on the examination object as low as possible.

The task of the invention is solved by a method for recording an examination object using an x-ray recording system rotatable about a common axis of rotation consisting of an x-ray source and an x-ray detector in accordance with the independent claim. Advantageous embodiments of the invention are in each case the subject matter of the associated dependent claims.

This requires a method for recording an examination object using an x-ray recording system rotatable about a common axis of rotation, consisting of an x-ray source and an x-ray detector, whereby in a first rotation with a plurality of first angular positions of x-ray source and x-ray detector about the axis of rotation first x-ray images are recorded, whereby the x-ray detector is arranged in such a way that it is displaced in a first direction so that the perpendicular bisector from the x-ray source to the x-ray detector in conjunction with a plane running through the x-ray source and containing the axis of rotation encloses a first angle $k \neq 0$ and in a second rotation with a plurality of second angular positions of x-ray source and x-ray detector about the axis of rotation second x-ray images are recorded, whereby the x-ray detector is arranged in such a way that it is displaced in a second direction so that the perpendicular bisector from the x-ray source to the x-ray detector in conjunction with a plane running through the x-ray source and containing the axis of rotation encloses a second angle $m \neq 0$, whereby the second angle is on the opposite side of the plane from the first angle k. This is the large-volume method i.e. an x-ray acquisition with in each case a first rotation with an x-ray detector displaced to the left and a second rotation with an x-ray detector displaced to the right about the axis of rotation. In accordance with the invention, in this method the first and second rotations span between their starting point and their finishing point in each case at most, in particular precisely, angular ranges of $\pi+\beta_0$ and differ from each other in their starting points by an angle of displacement $\beta_0$, whereby the angle of displacement is $$\beta_0 = \frac{k+m+d}{2},$$

where d is the detector fan angle spanned by the x-ray detector in relation to the x-ray source. This means that the doubled displacement angle $2\beta_0$ is the fan angle spanned by the so-called virtual x-ray detector. The basis for the invention is the knowledge that in the known recording methods, in which angular ranges of at least $\pi+2\beta_0$ are traveled for each rotation, areas are measured twice, which causes an unnecessary radiation loading for the examination object.

Through the reduced rotations in the method in accordance with the invention by at least one angle of rotation of $\beta_0$ compared with the known acquisition methods a distinctly lower x-ray dose is applied to the examination object. As a result the radiation loading for the patient and for the examining personnel is reduced. Furthermore, through the method in accordance with the invention a 360° rotation does not have to be performed, which means that the examination procedure is much less complex.

In accordance with one embodiment of the invention the first angle k is less than or equal to half the angle of displacement. This means that in an envisaged juxtaposition of the x-ray detector displaced in the first direction with the x-ray detector displaced in the second direction, and with the x-ray source in the same position, they form an overlap (less than) or abut directly with each other (equal to).

Advantageously for a simple reconstruction of a 3D image of the examination object, in each case a first x-ray image is combined with in each case a second x-ray image, recorded with the x-ray source in the same position, to create in each case a total image.

In accordance with a further embodiment of the invention a 3D back projection of the x-ray images is performed to produce a 3D reconstruction. Total images as well as individual x-ray images can be included in this.

BRIEF DESCRIPTION OF THE DRAWINGS

The invention as well as further advantageous embodiments in accordance with features of the dependent claims is explained in more detail below with reference to schematically presented exemplary embodiments in the drawing, without the invention being limited to these exemplary embodiments:

DETAILED DESCRIPTION OF THE INVENTION

Using flexible C-arm x-ray devices x-ray images can be recorded during a common rotation of an x-ray source Q and an x-ray detector D about an axis of rotation A (mostly in the area of the examination object) and used for a tomographic reconstruction. In the known large-volume method for recording 3D images of particularly large examination objects O the recording range is increased by recording two x-ray images for each position of the x-ray source Q using an x-ray detector D displaced in two different, opposite directions (e.g. to the "left" and to the "right"). This is frequently carried out by means of two consecutive rotations, whereby in the first rotation the x-ray detector is displaced in a first direction (e.g. to the left) and in the second rotation is displaced in the opposite second direction (e.g. to the right). The two x-ray images can then be combined to create a total image and the plurality of various total images can be reconstructed to form a 3D image.

Figure 1:
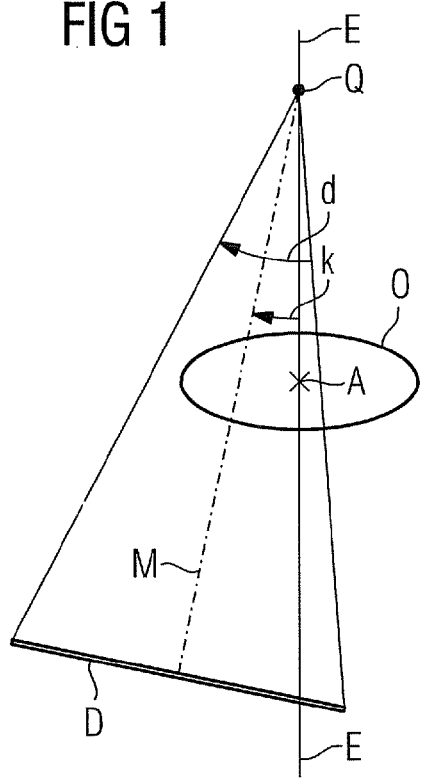
FIG. 1 is a view of the beam geometry in a first angular position with the x-ray detector displaced to the "left" in the prior art.
Figure 2:
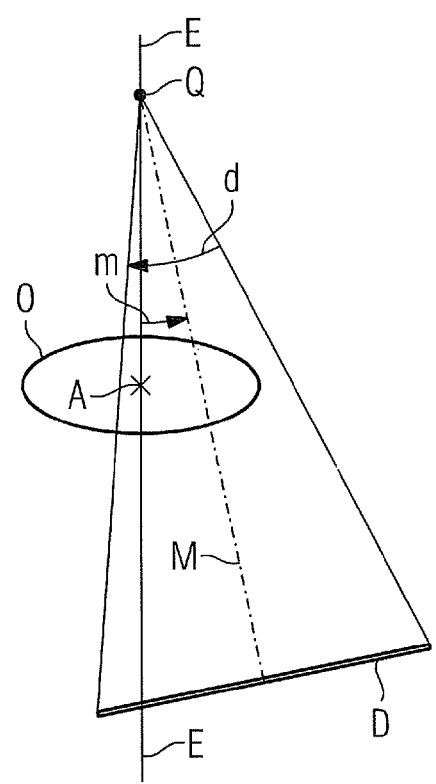
FIG. 2 is a view of the beam geometry in a second angular position with the x-ray detector displaced to the "right" in the prior art.

In FIG. 1 and FIG. 2 the recording geometries are shown for the displaced x-ray detector D and the matching position of the x-ray source Q. In FIG. 1 the x-ray detector D is displaced in the first direction (to the "left"), which means that the perpendicular bisector M from the x-ray source Q to the x-ray detector D in conjunction with a plane E running through the x-ray source Q and containing the axis of rotation A encloses a first angle $k \neq 0$. The detector fan angle d is spanned in relation to the x-ray source by the x-ray detector. In FIG. 2 the x-ray detector D is displaced in the second direction (to the "right"), which means that the perpendicular bisector M in conjunction with the plane E running through the x-ray source Q and containing the axis of rotation A encloses a second angle $m \neq 0$, which is on the opposite side of the plane E from the first angle k.

Figure 5:
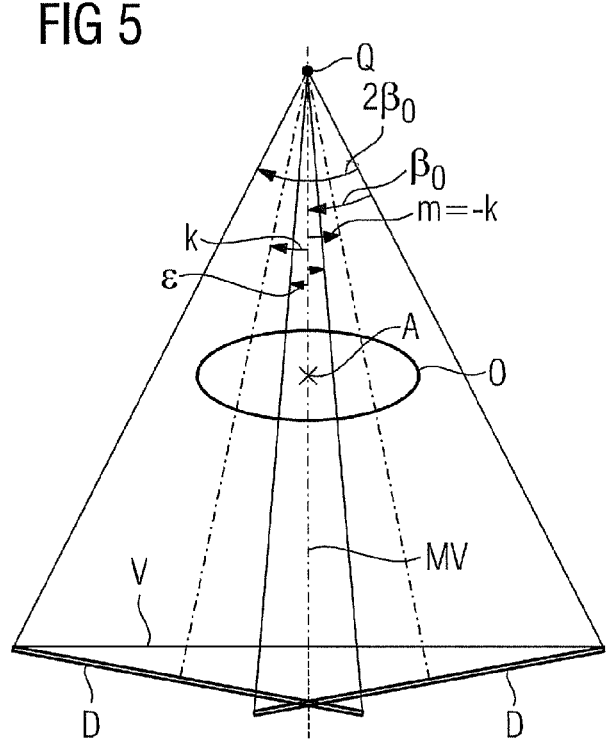
FIG. 5 is a view of the beam geometry in a combination of the angular positions as in FIG. 1 and FIG. 2 in the prior art.

In general it is usual for the second angle m to be of the same amount as the first angle k. Altogether it is also usual for the two angles to be less than or equal to half the detector fan angle d so that there are no gaps between the respective x-ray images. If they are to abut flush with each other, the two angles are selected as being equal to half the detector fan angle d. If an overlap $2\epsilon$ is required, the two angles are selected as being less than half the detector fan angle d. In FIG. 5 the recording geometry for both displaced positions of the x-ray detector D is shown, whereby a thus arising virtual detector V, a perpendicular bisector of the virtual detector MV and a virtual fan angle $2\beta_0$ spanned by the virtual detector in relation to the energy source Q are shown.

Figure 3:
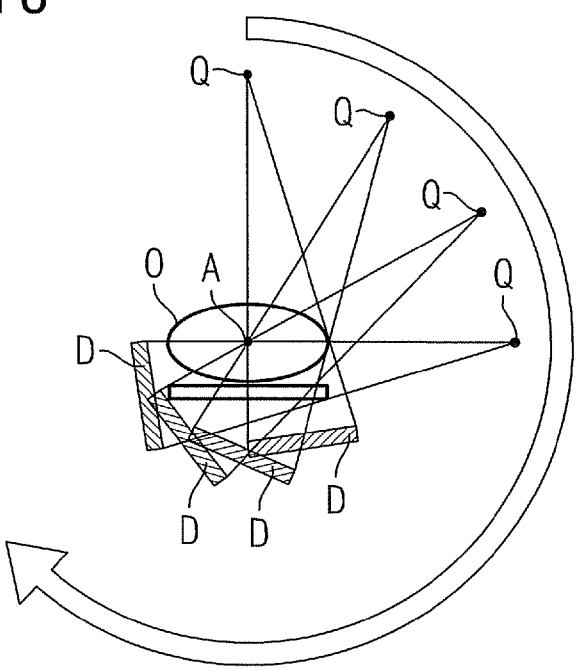
FIG. 3 is a view of several second angular positions as in FIG. 2 of a second rotation in the prior art.
Figure 4:
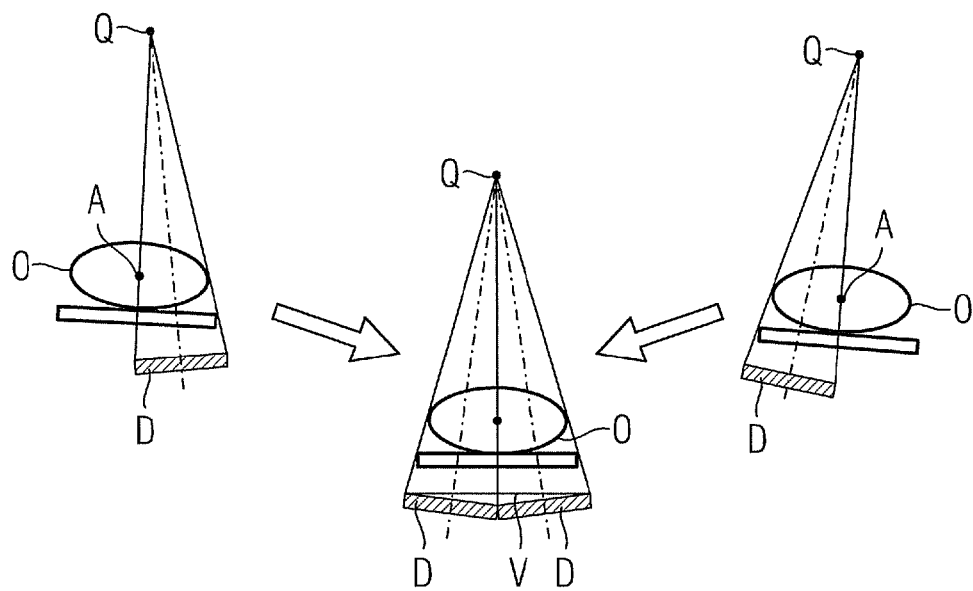
FIG. 4 is a view of a combination of a first angular position of the x-ray detector with a second angular position to fond a virtual detector in the prior art.

FIG. 3 shows how in a second rotation an x-ray detector D displaced by the second angle m (in this case m=d/2) rotates about the axis of rotation A, whereby second x-ray images are recorded in a plurality of positions. Likewise, in a first rotation an x-ray detector D displaced by the first angle k rotates about the axis of rotation A, whereby in a plurality of positions first x-ray images are recorded. In the prior art both the first rotation and the second rotation in each case span at least an angle of $\pi$ plus the virtual fan angle $2\beta_0$ about the axis of rotation A. FIG. 4 shows how first and second x-ray images recorded in each case in the first position of the x-ray source are combined, which thus makes it possible to reconstruct a complete image of the examination object O.

Figure 6:
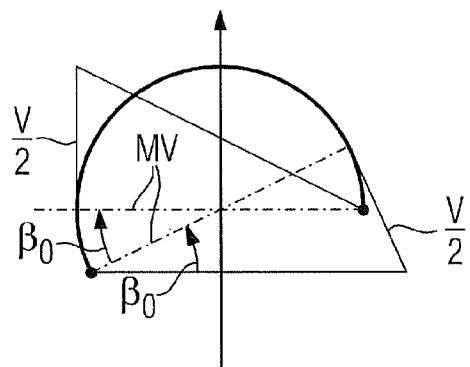
FIG. 6 is a view of the first rotation in the method in accordance with the invention.
Figure 7:
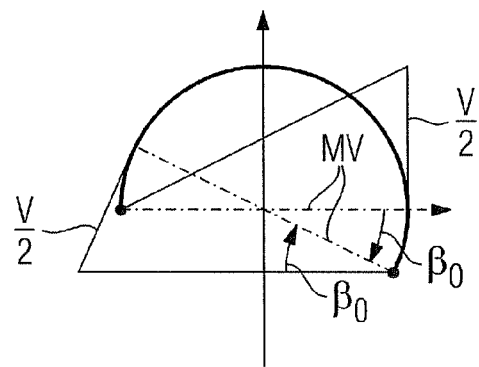
FIG. 7 is a view of the second rotation in the method in accordance with the invention.
Figure 10:
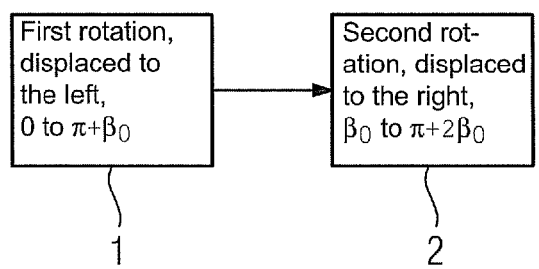
FIG. 10 is a sequence of the basic steps of the method in accordance with the invention.

Through the method in accordance with the invention the known method (FIG. 1 to FIG. 5) is now modified in such a way that a lower amount of x-ray dose is emitted onto the examination object. This is achieved by the fact that in the two rotations smaller angular ranges are traveled than in the prior art. FIGS. 6 and 7 show the angular ranges spanned about the axis of rotation by the first and second rotations in the method in accordance with the invention. In addition, they show (for the case k=d/2 and m=−k) in each case the x-ray beams emitted by the x-ray source onto half the virtual detector as well as the perpendicular bisector of the virtual detector MV for the respective starting points and finishing points of the rotations. FIG. 10 shows the most important steps in the method in accordance with the invention. In a first step 1 a first rotation is performed about the axis of rotation A over an angular range of $\pi+\beta_0$ (180° plus half the virtual fan angle) with the x-ray detector displaced to the left. Then in a second step a second rotation about the axis of rotation A is performed over an angular range of $\pi+\beta_0$ (180° plus half the virtual fan angle) with the x-ray detector displaced to the right, whereby the displacement between the starting points of the first rotation and the second rotation amounts to $\beta_0$. Thus, for example, the first rotation is performed from 0° to $\pi+\beta_0$ and the second rotation from $\beta_0$ to $\pi+2\beta_0$. If therefore the virtual fan angle amounts, for example, to $2\beta_0=40°$, in the method in accordance with the invention an angle of 200° is traveled for each rotation, whereas in known methods always at least 220° is traveled. In this case for example the x-ray dose is therefore reduced by about 10%.

Advantageously the first angle k and the second angle m are of the same amount. Moreover, it is advantageous if the first angle k is less than or equal to half the angle of displacement, and likewise the second angle m. This means that in an envisaged juxtaposed arrangement of the x-ray detector that is displaced in the first direction with the x-ray detector that is displaced in the second direction, and with the x-ray source in the same position, an overlap is created (k<d/2, likewise m) or a flush abutment takes place (k=d/2, likewise m).

Advantageously for a simple reconstruction of a 3D image of the examination object, if two x-ray images exist in each case a first x-ray image is combined with in each case a second x-ray image, recorded with the x-ray source in the same position, to form a total image.

Then, to produce a 3D image of the examination object, a 3D reconstruction of all the x-ray images can be performed. To do so, preferably the already combined total images are used. The 3D reconstruction can, for example, be performed by means of a known 3D back projection. Total images as well as individual x-ray images can be included for this.

Figure 8:
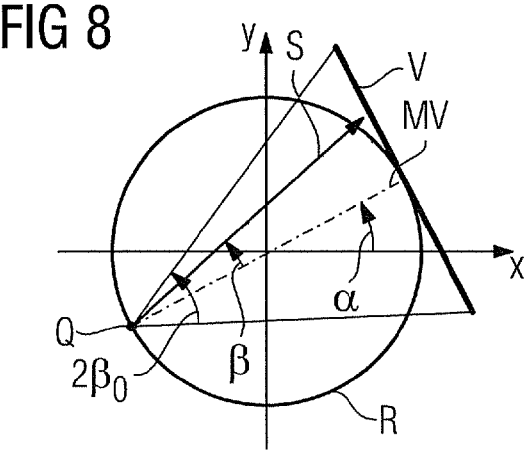
FIG. 8 is a view of the beam geometry during a rotation.
Figure 9:
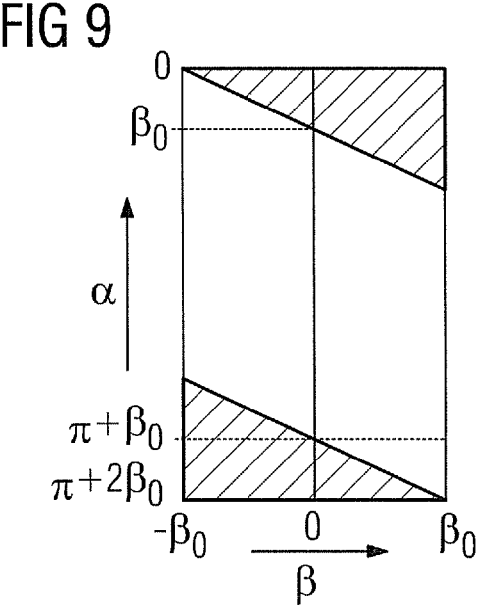
FIG. 9 is a function to indicate the areas measured twice.

The invention is based on the knowledge that in the known methods in the prior art some angular ranges are measured twice and therefore unnecessarily. This is shown in FIG. 8 and FIG. 9. FIG. 8 shows the geometry of the rotations about the axis of rotation by means of the system of coordinates consisting of the x-axis and y-axis, whereby instead of the displaced x-ray detector the virtual detector V with the perpendicular bisector of the virtual detector MV is shown. The angle between the perpendicular bisector of the virtual detector MV and the x-axis is designated as $\alpha$, the angle between the measurement beam S and the perpendicular bisector of the virtual detector MV is designated as $\beta$. If in a system of coordinates $\alpha$ is plotted against $\beta$ (vid. FIG. 9), it can be seen that some areas (hatched) are measured twice. From the article by Dennis L. Parker, "Optimal short scan convolution reconstruction for fanbeam CT", Med. Phys. 9 (2), March/April 1982, pp. 254-257, it is also known for a normal x-ray detector positioned symmetrically in relation to the axis of rotation that areas are measured twice. In the known case they still have to be measured because it is technically problematic to just read off half of an x-ray detector. In the present case it is, however, possible unproblematically to dispense with using half of the "virtual" total images as the first x-ray image and the second x-ray image from which a total image is composed were recorded separately from each other.

If diaphragms are additionally inserted in the beam area to mask the beams that are not required, the applied dose can be reduced by a further approx. 10%, so that also with the mechanically restricted systems dose-reducing recordings can be made of an expanded measurement field.

The invention can be summarized briefly as follows: To keep the radiation loading as low as possible while recording a 3D x-ray image that is as large as possible, a method is provided for recording an examination object using an x-ray recording system rotatable about a common axis of rotation A, which system consists of an x-ray source Q and an x-ray detector D, whereby in a first rotation with a plurality of first angular positions of x-ray source Q and x-ray detector D about the axis of rotation A first x-ray images are recorded, whereby the x-ray detector is arranged in such a way that it is displaced in a first direction so that the perpendicular bisector from the x-ray source to the x-ray detector in conjunction with a plane running through the x-ray source Q and containing the axis of rotation A encloses a first angle k≠0 and in a second rotation with a plurality of second angular positions of x-ray source Q and x-ray flat detector D about the axis of rotation A second x-ray images are recorded, whereby the x-ray detector is arranged such that it is displaced in a second direction so that the perpendicular bisector M from the x-ray source to the x-ray detector in conjunction with a plane E running through the x-ray source Q and containing the axis of rotation A encloses a second angle m≠0, whereby the second angle is on the opposite side of the plane from the first angle k, whereby the first and the second rotations about the axis of rotation span between their starting points and their finishing points in each case at most, in particular precisely, angular ranges of $\pi+\beta_0$ and differ in their starting points by an angle of displacement $\beta_0$, whereby the angle of displacement is $$\beta_0 = \frac{k+m+d}{2},$$

where d is the detector fan angle spanned by the x-ray detector in relation to the x-ray source.

The invention claimed is:

1. A method for recording an examination object using an x-ray recording system having an x-ray source and an x-ray detector rotatable about a common axis of rotation, comprising:
    displacing the x-ray detector in a first direction to enclose a first angle k between a perpendicular bisector from the x-ray source to the x-ray detector and a plane running through the x-ray source and containing the common axis of rotation, wherein the first angle k≠0;
    recording a first plurality of x-ray images during a first rotation about the common axis of rotation in a first plurality of angular positions of the x-ray source and the x-ray detector displaced in the first direction;
    displacing the x-ray detector in a second direction to enclose a second angle m between the perpendicular bisector and the plane, wherein the second angle m≠0 and is on an opposite side from the first angle k; and
    recording a second plurality of x-ray images during a second rotation about the common axis of rotation in a second plurality of angular positions of the x-ray source and the x-ray detector displaced in the second direction,
    wherein starting points of the first and the second rotations about the common axis of rotation are differed by an angle of displacement $\beta_0$,
    wherein the starting points and finishing points of the first and the second rotations about the common axis of rotation are spanned by an angle $\pi+\beta_0$, and
    wherein the angle of displacement $$\beta_0 = \frac{k+m+d}{2},$$

wherein d is a fan angle of the detector spanned by the x-ray detector in relation to the x-ray source.

2. The method as claimed in claim 1, wherein the first angle is less than or equal to half of the angle of displacement.

3. The method as claimed in claim 1, wherein one of the first x-ray images is combined with one of the second x-ray images recorded with the x-ray source in a same angular position to form a total image.

4. The method as claimed in claim 3, wherein the first and the second angles are selected so that the one of the first x-ray images overlaps with the one of the second x-ray images to be combined with the one of the first x-ray images.

5. The method as claimed in claim 1, wherein the first and the second x-ray images are reconstructed by a 3D back projection to produce a 3D reconstruction.

* * * * *